United States Patent [19]
Pino y Torres

[11] Patent Number: 4,554,909
[45] Date of Patent: Nov. 26, 1985

[54] VAGINAL APPLICATOR

[76] Inventor: Jose L. Pino y Torres, 918 Versailles Cir., Maitland, Fla. 32751

[21] Appl. No.: 498,919

[22] Filed: May 27, 1983

[51] Int. Cl.$^4$ .............................................. A61J 1/00
[52] U.S. Cl. .................................................... 128/1.2
[58] Field of Search ................. 128/1.2, 1.1, 788, 804, 128/127, 128

[56] References Cited

U.S. PATENT DOCUMENTS

| 3,789,829 | 2/1974 | Hasson | 128/1.2 |
| 3,807,386 | 4/1974 | Rocoplan et al. | 128/1.2 |
| 4,244,357 | 1/1981 | Morrison | 128/1.2 |
| 4,292,960 | 10/1981 | Paglione | 128/1.2 |
| 4,294,264 | 10/1981 | Fischell et al. | 128/1.2 |
| 4,331,131 | 5/1982 | Kumar | 128/1.2 |

OTHER PUBLICATIONS

Haybittle et al., "A Simple After-Loading . . . Cervix", Br. J. Rad, vol. 48, 568: 295-298, 4/1975.

Primary Examiner—Lee S. Cohen
Assistant Examiner—Steven Falk
Attorney, Agent, or Firm—Cushman, Darby & Cushman

[57] ABSTRACT

A therapeutic instrument, and method, for radiation treatment of patients with carcinoma of the cervix and uterus. An elongated uterovaginal tandem having a curved proximal end is inserted in the uterine cavity, and an intravaginal applicator having a bore receiving the tandem is slid over the tandem into the vagina, and the tandem and applicator are fixed so that no relative motion therebetween is possible. The applicator obviates the need for packing of the vagina, having a quadrate cross-section, with rounded corners that substantially fills the vagina if the appropriate size of applicator is selected. Sutures are used to connect the distal end of the applicator adjacent the vaginal introitus. The applicator is then loaded with a pair of containers of irradiative material, the containers inserted utilizing handles through passageways in the applicator to cavities in the applicator on either side of the tandem and adjacent the slanted proximal end of the applicator. The tandem is located with respect to the applicator cavities so that a greater distance is provided between the irradiative material containers and the vaginorectal septum.

16 Claims, 6 Drawing Figures

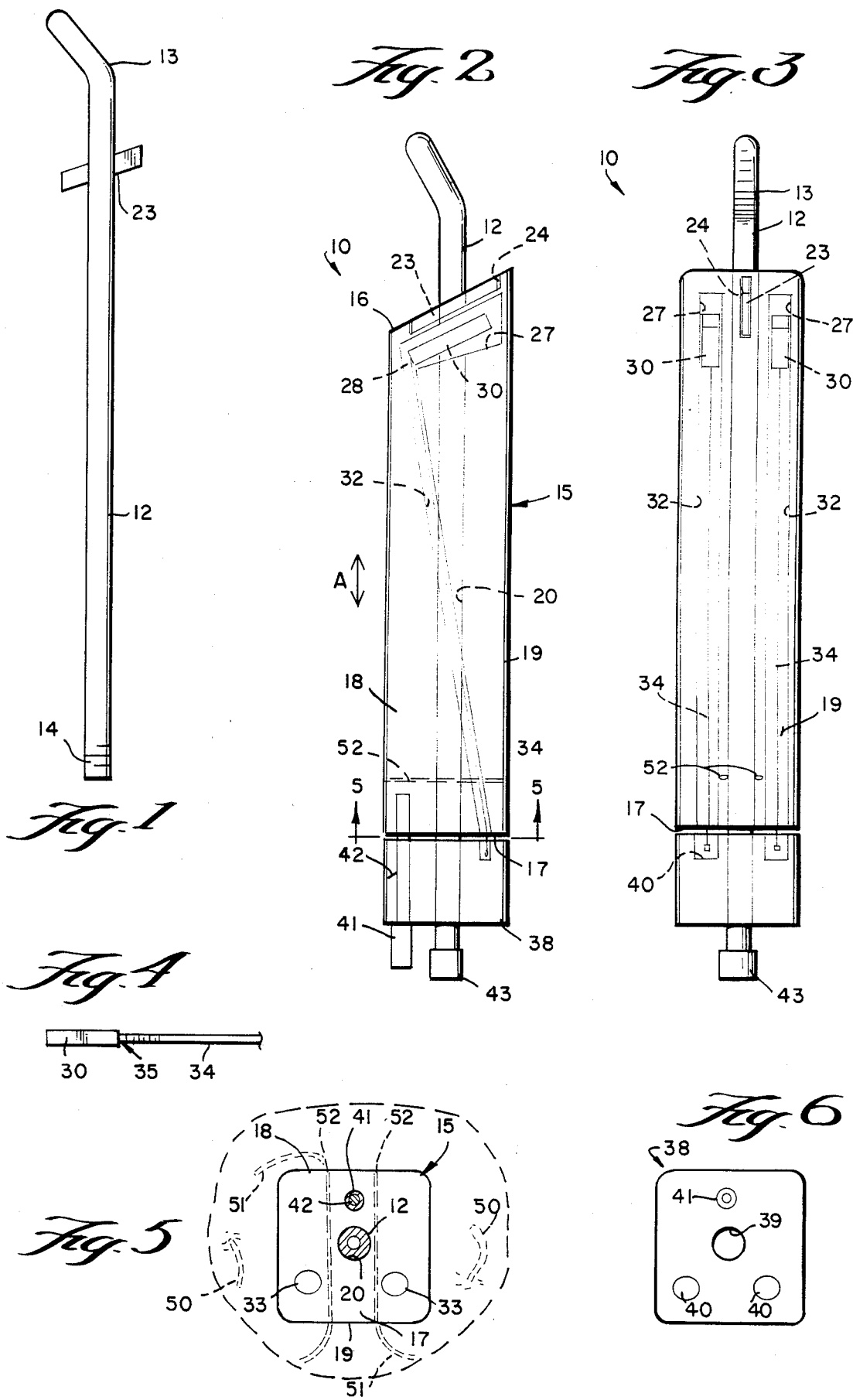

VAGINAL APPLICATOR

BACKGROUND AND SUMMARY OF THE INVENTION

Conventional procedures utilizing conventional instruments for irradiative treatment of the genital tract of patients with carcinoma of the cervix and uterus are complex and time consuming. The most common conventional treatment method includes utilization of what is known in the trade as the Fletcher-Suit after-loading applicator and Delclos after-load mini-ovoids. The placement of the applicator ovoid in relation to the tandem is time consuming and difficult especially in patients with narrow vaginas or a distorted anatomy. Also X-rays are required during surgery after placement of the applicator to check its correct placement, and the patient requires bed rest with minimal motion during the duration of the irradiation treatment (usually two to three days). Motion of the patient in bed may displace the applicator, which requires a return to the operating room for correct replacement. Also the frequency of checking the placement of the irradiative sources exposes the hospital personnel to an undesired frequency of exposure to the radiation. While an experienced physician can properly place a Fletcher-Suit applicator in a patient with normal anatomy in 15-30 minutes, because the skills necessary can be acquired only through extensive training, procedures as long as 3½ hours for correct placement of the applicator have been required, with corresponding increased time that the patient is under anesthesia and with corresponding increased risk to the patient.

The instrument, and method, according to the present invention overcome most of the disadvantages associated with conventional procedures for treatment of patients with carcinoma of the cervix and uterus. The intravaginal applicator according to the present invention is constructed so that no packing of the vagina is required, saving anesthesia time. Further, suturing of the applicator to the patient at the vaginal introitus ensures that the applicator will remain in proper position despite normal movements of the patient in bed during the duration of the irradiative treatment so that constant checking and/or re-placement of the applicator are usually avoided. Additionally, the location of the irradiative material - in practicing the invention - is extremely precise, and minimizes the chance of involvement of the vaginorectal septum, with corresponding minimized risk of complication. Also, the method according to the invention is much simplified compared to normal procedures, providing simplified training of medical personnel, and minimized placement times.

The instrument according to the present invention includes a tandem having a curved proximate end. The terms "proximal" and "distal" as used in the present specification and claims are relative to the patient's genital tract. That is a "proximal" position is closer to the area to be treated in the genital tract, while a "distal" location is closer to the vaginal introitus (entrance).

The instrument according to the invention also includes an intravaginal applicator. The applicator is preferably quadrate in cross-section, having rounded corners, and has a bore formed along the dimension of elongation thereof for receipt of the tandem. The bore is preferably slightly closer to the anterior surface of the applicator than the posterior surface thereof, to minimize the probability of involvement of the vaginorectal septum. The terms "anterior" and "posterior" as used in the present specification and claims are also relative to the patient's genital tract. Thus an anterior location is closer to the front of the patient's body, while a posterior location is closer to the rear of the patient's body (e.g. rectum).

The applicator includes a slanted proximate end so that the posterior surface thereof is slightly longer than the anterior surface thereof. A pair of cavities are formed in the applicator adjacent the proximate end thereof, one disposed on either side of the tandem-receiving bore. A passageway extends from an opening at the distal end of the applicator adjacent the posterior surface thereof to the opening of each cavity, adjacent the anterior surface and proximal end of the applicator. After-loading of the system is accomplished by inserting a container of irradiative material in each cavity, insertion being accomplished utilizing a handle connected by a flexible hinge connection to each container.

A keel, or like means, is provided for preventing relative rotation between the applicator and tandem, and suture-receiving openings are formed at the distal end of the applicator. During the operative procedure inserting the applicator, sutures are provided at the vaginal introitus, and those sutures are operatively connected to sutures received by the applicator openings to thereby positively hold the applicator in place.

Subsequent to after-loading of the applicator with the irradiative material, a cap is operatively attached to the applicator, closing off the opening at the distal end thereof, and receiving the tandem therein.

It is the primary object of the present invention to provide a simple and effective instrument and method for facilitating the treatment of patients with carcinoma of the cervix and uterus, or like conditions. This and other objects of the invention will become clear from an inspection of the detailed description of the invention, and from the appended claims.

BRIEF DESCRIPTION OF THE DRAWINGS

FIG. 1 is a side view of an exemplary tandem according to the present invention;

FIG. 2 is a side view of an exemplary instrument according to the present invention, the applicator being shown as being of transparent material for clarity of illustration;

FIG. 3 is a plan view of the instrument of FIG. 2 looking in at the posterior end thereof;

FIG. 4 is a detail side view showing the interconnection between an exemplary container and handle for after-loading of the instrument with irradiative material;

FIG. 5 is a cross-sectional view taken along line 5—5 of FIG. 2, and showing—in dotted line—operative positioning of the instrument with respect to a vaginal introitus, with sutures also being shown in dotted line; and FIG. 6 is a plan view of the cap of the instrument of FIG. 2.

DETAILED DESCRIPTION OF THE DRAWINGS

An exemplary instrument according to the present invention is shown generally by reference 10 in FIGS. 2 and 3. One of the main components of the instrument comprises an elongated uterovaginal tandem 12, shown most clearly in FIGS. 1 through 3. The tandem 12 includes a curved proximate end 13, and a distal end 14 which may have exterior screw threads associated therewith. Preferably the tandem 12 is circular in cross-section, as seen most clearly in FIG. 5, and is tubular. The tandem preferably is made out of metal.

Another major component of the instrument 10 according to the invention comprises an enlarged intravaginal applicator 15. The applicator 15 may be made of any inert material, such as a wide variety of plastics. For clarity of illustration (only) in FIGS. 2 and 3 the applicator 15 is shown as being of transparent material.

The applicator 15 includes a slanted proximate end 16, and a distal end 17 that is generally perpendicular to the dimension of elongation A (see FIG. 2) thereof. For maximum utility, the applicator 15 is preferably quadrate (i.e. square or rectangular) in cross-section, as can be seen most clearly in FIG. 5, and the corners thereof are rounded, as is also clearly seen in FIG. 5. The applicator 15 is dimensioned so that it can be placed in the patient's vagina without the necessity of accessory packing. This can be seen from the schematic illustration in FIG. 5.

The applicator 15 includes an anterior surface 18 thereof, and a posterior surface 19, and a bore 20 (see FIGS. 2 and 5) elongated in the dimension A. While the bore 20 may be at the geometric center of the applicator 15, preferably it is slightly off center, being slightly closer (e.g. 2 millimeters) to the anterior surface 18 than the posterior surface 19, as can be seen in FIG. 5. This minimizes the possibilities vaginorectal septum injury.

Means are provided for preventing relative rotation between the tandem 12 and applicator 15. One form such means can take comprises a keel 23 affixed to the tandem 12 (see FIGS. 1 through 3), with a cooperating channel 24 (see FIGS. 2 and 3) formed in the proximal end 16 of the applicator 15 for receipt of the keel 23. The keel 23 preferably is a plate of metal intersecting the tandem 12 and having the same slope as the proximal surface 16 of the applicator 15, and being flush with the applicator 15 when properly positioned with respect thereto (as shown in FIG. 2).

Means must be provided for after-loading the tandem-applicator system with irradiative treatment material, such as radium. This is preferably accomplished by providing at least one, and preferably a pair, of cavities 27 (see FIGS. 2 and 3) within the applicator 15 adjacent the distal end 17 thereof. The cavities 27 generally extend from the posterior surface 19 toward the anterior surface 18, with an entrance 28 adjacent the anterior surface 18, and the cavities 27 preferably are slanted in the same manner as the distal end 17 of the applicator 15. The cavities 27 are dimensioned to receive a container 30 of irradiative material. Preferably each container 30 is a cylinder.

The containers 30 may be inserted into the cavities 27 through elongated passageways 32. Each passageway 32 has an entrance opening 33 (see FIG. 5) at the distal end of the applicator 15 adjacent the posterior surface 19 thereof, and extends toward the cavity entrance 28 adjacent the anterior surface 18 and proximate end 16 of the applicator 15, as seen most clearly in FIG. 2. Insertion of the container 30 through the passageway 32 into the cavity 27 is accomplished utilizing an elongated handle 34, the handle 34 having a length slightly greater than that of the passageway 32, and being interconnected to the container 30 with a conventional flexible hinge 35 (see FIG. 4), which maintains the container 30 and handle 34 in any relative angular position to which they are moved with respect to each other.

The instrument 10 finally includes a cap 38, as seen most clearly in FIGS. 2, 3, and 6. The cap 38 preferably is of the same inert material as the applicator 15 and has the same cross-section, as seen in FIG. 6. The cap 38 includes a bore 39 therethrough for receipt of the tandem 12 adjacent its distal end 14, and a pair of channels 40. The channels 40 receive the ends of the handles 34 extending outwardly from the applicator distal end 17, as seen in FIGS. 2 and 3. The cap 38 is interconnected to the applicator 15 by a female-ended bolt 41 which receives a male exteriorly threaded screw 42 (see FIG. 5) therein, the screw 42 extending in the dimension A outwardly from the distal end 17 of applicator 15. A nut 43 preferably is also screw threaded over the distal end 14 of the tandem 12.

Operation

An exemplary procedure utilizing the instrument 10 in practicing the method according to the invention will now be set forth. Conventional accessory procedures, such as inserting a catheter into the bladder, and the like, will not be described.

The physician does an examination of the patient to determine the correct size of instrument to be utilized. Generally four different sizes of applicators will accommodate the vast majority of patients, a typical applicator having a width of 4.5 centimeters, a height of 3.4 centimeters, with the radioactive containers 30 separated from each other at the end of the applicator by 2.7 centimeters, and the radioactive sources at the end of the applicator being 0.9 centimeters from the proximate end face 16 thereof. A number of different tandems, having different degrees of curvature of próximate ends 13, also may be utliized.

After determining the relevant dimensions of the patient's genital tract, the physician clamps the patient's cervix. Then the uterine cavity is sounded and dilated. A pair of sutures 50 (see FIG. 5) are then placed at the vagina introitus, and then the tandem 12 is inserted into the uterine cavity with the keel 23 properly positioned at the place determined by sounding of the uterine cavity.

The intravaginal applicator 15 is then introduced into the vagina, sliding over the tandem 12 with the tandem 12 received within the bore 20 therin, until the cavity 24 completely receives the keel 23. No packing operation is necessary. The applicator and tandem are checked so that it is determined that no relative rotation therebetween is possible. During insertion of the applicator 12, care is taken to make sure that the anterior surface 18 is positioned properly in the vagina.

After insertion of the applicator 15 the sutures 50 are operatively connected (e.g. tied) to sutures 51 (see FIG. 5) operatively connected to the applicator 15. Preferably each suture 51 is operatively connected to the applicator 15 by looping it through a passageway interconnecting a pair of openings 52 (see FIG. 5) formed in the distal end 17 of the applicator 15, although a wide variety of attachment mechanisms are utilizable.

After the applicator 15 is properly positioned and the sutures 50, 51 are tied together to positively hold the applicator in place, then loading of the tandem-applicator system is accomplished. This is done by inserting a container 30 into each passageway opening 33, and pushing it with a handle 34. The container 30 passes through passageway 32 and once it reaches the cavity entrance 28 it drops down into the cavity 27, the flexible hinge connection 35 between the handle 34 and container 30 allowing this action.

Subsequent to loading, the applicator 15 is capped. This is accomplished by passing the cap 38 over the tandem 12 so that the tandem 12 is received within bore 39 in cap 38, and screwing bolt 41 into operative association with bolt 42 so that the cap 38 is operatively held to the applicator 15. In this position the channels 40 receive the ends of the handles 34 extending outwardly from the applicator 15. The nut 43 may then be disposed over the distal end 14 of the tandem 12.

It will thus be seen that according to the present invention a simple and effective instrument and procedure have been provided for treatment of patients with carcinoma of the cervix and uterus, and like conditions. While the invention has been herein shown and described in what is presently conceived to be the most practical and preferred embodiment thereof, it will be apparent to those of ordinary skill in the art that many modifications may be made thereof with the scope of the invention, which scope is to be accorded the broadest interpretation of the appended claims so as to encompass all equivalent instruments and procedures.

What is claimed is:

1. An instrument for irradiative treatment of the genital tract, comprising:
   an elongated uterovaginal tandem having a curved proximal end, and a distal end;
   an enlarged intravaginal applicator elongated in a dimension of elongation, and a tandem-receiving bore formed therein along said dimension of elongation, said applicator also including a proximal end, a distal end, an anterior portion and a posterior portion;
   means for operatively interconnecting said tandem and said intravaginal applicator during use with said tandem received by said tandem-receiving bore so that relative rotational movement therebetween is prevented;
   means defining at least one cavity in said applicator adjacent the proximal end thereof, and means defining a passageway extending from said cavity to the distal end of said applicator, said passageway and cavity for receipt of a container of irradiative treatment material; and
   means defining suture receiving openings at said distal end of said intravaginal applicator.

2. An instrument as recited in claim 1 further comprising means defining suture receiving openings at said distal end of said intravaginal applicator.

3. An instrument as recited in claim 1 wherein said applicator is essentially quadrate in cross-section, having rounded corners.

4. An instrument as recited in claim 3 wherein said tandem-receiving bore in said intravaginal applicator is non-concentric, being located closer to said anterior portion of said applicator than said posterior portion thereof.

5. An instrument as recited in claim 4 further comprising a cap, and means for attaching said cap to said distal end of said applicator with said cap receiving said distal end of said tandem therein, and closing off the open end of said passageway in said applicator.

6. An instrument as recited in claim 3 wherein said proximal end of said applicator is slanted so that said applicator has a longer posterior surface than anterior surface, and wherein said cavity is dimensioned so that it is generally parallel to said slanted proximal end of said applicator.

7. An instrument as recited in claim 6 wherein said means defining at least one cavity and said passageway comprises means defining a pair of cavities and a pair of passsageways, one cavity and cooperating passageway being disposed on either side of said tandem-receiving bore; and wherein each of said passageways extends from a position at said distal end of said applicator adjacent said posterior surface thereof to a cavity opening adjacent said proximal end of said applicator and adjacent said anterior surface thereof.

8. An instrument as recited in claim 7 further comprising a pair of containers of irradiative material, each container generally comprising a cylinder disposed in a respective said cavity; a handle for inserting each container into said cavity, each said handle having a length slightly greater than the length of one of said passageways; and flexible hinge means interconnecting each said handle and said container.

9. An instrument as recited in claim 8 further comprising a cap, said cap having a bore therein receiving said distal end of said tandem, and said cap operatively interconnected to said applicator at said distal end of said applicator; and means defining a pair of channels in said cap for receipt of portions of said handles extending outwardly from said applicator.

10. A therapeutic instrument for irradiative treatment of the genital tract comprising:
    an elongated uterovaginal tandem having distal and proximal ends;
    an enlarged intravaginal applicator elongated in a dimension of elongation and having a tandem-receiving bore formed therein in said dimension of elongation thereof, said applicator having a slanted proximal end, a distal end, an anterior portion, and posterior portion;
    means for operatively interconnecting said tandem and said intravaginal applicator during use with said tandem received by said tandem-receiving bore so that relative rotational movement therebetween is prevented;
    means defining a pair of cavities for receipt of containers of irradiative material adjacent said applicator proximal end, one cavity disposed on either side of said tandem-receiving bore and generally extending from adjacent said posterior portion to adjacent said anterior portion;
    means defining an elongated passageway associated with each cavity, each pasageway extending from an entrance at said applicator distal end adjacent said posterior portion to an opening for said cavity adjacent said anterior portion and proximal end of said applicator;
    a pair of containers containing irradiative material and disposed in respective said cavities;
    a handle for each container, each handle having a length slightly greater than the length of a cooperating passageway;
    flexible hinge means interconnecting each container and handle; and
    a cap operatively attached to said distal end of said applicator.

11. An instrument as recited in claim 10 further comprising means defining suture receiving openings at said distal end of said intravaginal applicator.

12. An instrument for irradiative treatment of the genital tract, comprising:

an elongated uterovaginal tandem having a curved proximal end, and a distal end;

an enlarged intravaginal applicator elongated in a dimension of elongation, and a tandem-receiving bore formed therein along said dimension of elongation, said applicator also including a proximal end, a distal end, an anterior portion and a posterior portion; said applicator being a substantially continuous body that is essentially quadrate in cross-section, and has rounded corners;

means for operatively interconnecting said tandem and said intravaginal applicator during use with said tandem operatively received by said tandem-receiving bore so that relative rotational movement therebetween is prevented; and means defining at least one cavity in said applicator adjacent the proximal end thereof, and means defining a passageway extending from said cavity to the distal end of said applicator, said passageway and cavity for receipt of a container of irradiative treatment material.

13. A method of treating a patient having carcinoma of the cervix and uterus, or a like condition, comprising the steps of:
 (a) examining the patient to determine relevant dimensions of the patient's genital tract;
 (b) clamping the cervix;
 (c) sounding and dilating the uterine cavity;
 (d) placing sutures in the patient at the vaginal introitus;
 (e) selecting an appropriate tandem and vaginal applicator based upon the results of the examination in step (a);
 (f) introducing the selected tandem in the uterine cavity;
 (g) without packing the vagina, introducing the selected vaginal applicator into the vagina with the applicator receiving the tandem therearound, the applicator essentially providing the packing for the vagina;
 (h) connecting the sutures at the vaginal introitus to sutures operatively connected to a distal end of the applicator; and then
 (i) loading the applicator with irradiative material for subjecting desired portions of the genital tract to irradiation.

14. A method as recited in claim 13 wherein steps (f) and (g) are practiced so that there is no relative rotatable movement between the tandem and applicator once properly inserted.

15. A method as recited in claim 13 wherein step (i) is practiced by inserting at least one container of irradiative material through a passageway in the applicator opening to the distal end of the applicator, and lodging the container in a cavity formed in the applicator adjacent a proximal end of the applicator.

16. A method as recited in claim 13 comprising the further step of capping the distal end of the applicator.

* * * * *